United States Patent [19]
Dunlay et al.

[11] Patent Number: 5,989,835
[45] Date of Patent: Nov. 23, 1999

[54] SYSTEM FOR CELL-BASED SCREENING

[75] Inventors: R. Terry Dunlay; D. Lansing Taylor, both of Pittsburgh, Pa.

[73] Assignee: Cellomics, Inc., Pittsburgh, Pa.

[21] Appl. No.: 08/810,983

[22] Filed: Feb. 27, 1997

[51] Int. Cl.⁶ .................................................. G01N 33/533
[52] U.S. Cl. ......................... 435/7.2; 435/7.21; 435/29; 435/40.5; 435/40.51; 435/288.3; 435/288.4; 436/546; 436/172; 436/800; 436/809
[58] Field of Search ...................................... 435/7.2, 7.21, 435/29, 40.5, 40.51, 288.3, 288.4; 436/546, 172, 800, 809

[56] References Cited

U.S. PATENT DOCUMENTS

| | | | |
|---|---|---|---|
| 5,355,215 | 10/1994 | Schroeder et al. ...................... | 356/317 |
| 5,401,629 | 3/1995 | Harpold et al. . | |
| 5,436,128 | 7/1995 | Harpold et al. . | |
| 5,491,084 | 2/1996 | Chalfie et al. . | |
| 5,548,661 | 8/1996 | Price et al. .............................. | 382/133 |

FOREIGN PATENT DOCUMENTS

| | | |
|---|---|---|
| WO 87 02802 | 7/1987 | WIPO . |
| WO 94 11841 | 5/1994 | WIPO . |
| WO 95/07463 | 3/1995 | WIPO . |
| WO 95/21191 | 8/1995 | WIPO . |
| WO 96/23898 | 8/1996 | WIPO . |
| WO 96/27675 | 9/1996 | WIPO . |

OTHER PUBLICATIONS

Bhatia et al., "Fabrication of Surfaces Resistant to Protein Adsorption and Application to Two–Dimensional Protein Patterning," Analytical Biochemistry 208:197–205 (1993).

Calvert et al., "Photoresist Channel–Constrained Deposition of Electroless Metallization on Ligating Self–Assembled Films," Journal of Vacuum Science and Technology B12:3884–3997 (1994).

Calvert, "Lithographically Patterned Self–Assembled Films," In Thin Films, vol. 20: Organic Thin Films And Surfaces:Directions For The Nineties, A. Ulman, Ed., Academic Press, Boston, pp. 109–141 (1995).

(List continued on next page.)

*Primary Examiner*—Christopher L. Chin
*Assistant Examiner*—Bao-Thuy L. Nguyen
*Attorney, Agent, or Firm*—David S. Harper; McDonnell Boehnen Hulbert & Berghoff

[57] ABSTRACT

The invention relates to an optical system for determining the distribution, environment, or activity of fluorescently labeled reporter molecules in cells for the purpose of screening large numbers of compounds for specific biological activity. The invention involves providing cells containing fluorescent reporter molecules in an array of locations and scanning numerous cells in each location with a fluorescent microscope, converting the optical information into digital data, and utilizing the digital data to determine the distribution, environment or activity of the fluorescently labeled reporter molecules in the cells. The array of locations may be an industry standard 96 well or 384 well microtiter plate or a microplate which is a microplate having a cells in a micropaterned array of locations. The invention includes apparatus and computerized method for processing, displaying and storing the data.

8 Claims, 10 Drawing Sheets

OTHER PUBLICATIONS

Chalfie et al., "Green Fluorescent Protein as a Marker For Gene Expression," Science 26:12501–12504 (1994).

Chrisey et al., Selective Attachment of Synthetic DNA to Self–Assembled–Monolayer Functionalized Surfaces, Proceedings, Materials Research Society 330:179–184 (1994).

Chrisey et al., "Covalent Attachment of Synthetic DNA to Self–Assembled Monolayer Films," Nucleic Acids Research 24:3031–3039 (1996).

Chrisey et al., "Fabrication of Patterned DNA Surfaces," Nucleic Acids Research 24:3040–3047 (1996).

Davis et al., "A Nuclear GFP That Marks Nuclei in Living Drosophila Embryos; Maternal Supply Overcomes a Delay in the Appearance of Zygotic Fluorescence," Dev. Biology 170:726–729 (1995).

Dulcey et al., "Deep UV Photochemistry of Chemisorbed Monolayers: Patterned Coplanar Molecular Assemblies," Science 252:551–554 (1991).

Dulcey et al., "Photochemistry and Patterning of Self–Assembled Monolayer Films Containing Aromatic Hydrocarbon Functional Groups," Langmuir 12:1638–1650 (1996).

Firestone et al., "Comparison of Autofocus Methods for Automated Microscopy," Cytometry 12:195–206 (1991).

Groen et al., "A Comparison of Different Focus Functions for Use in Autofocus Algorithms," Cytometry 6:81–91 (1985).

Harms and Aus, "Comparison of Digital Focus Criteria for a TV Microscope System," Cytometry 5:236–243 (1984).

Hu and Cheng, "Expression of Aequorea Green Fluorescent protein in Plant Cells," FEBS Letters 369:331–334 (1995).

Kaether and Gerdes, "Visualization of Protein Transport Along the Secretory pathway Using Green Fluorescent Protein," FEBS Letters 369:267–271 (1995).

Kapur et al., "Fabrication and Selective Surface Modification of 3–Dimensionally Textured Biomedical Polymers from Etched Silicon Substrates," Journals of Biomedical Materials Research 33:205–216 (1996).

Kittler et al., "Threshold Selection Based on a Simple Image Statistic," in Computer Vision, Graphics and Image Processing 30:125–147 (1985).

Morise et al., "Intermolecular Energy Transfer in the Bioluminescent System of Aequorea," Biochemistry 13:2656–2662 (1974).

Proffitt et al., "A Fluorescence Digital Image Microscopy System for Quantifying Relative Cell Numbers in Tissue Culture Plates," Cytometry 24:204–213 (1996).

Ridler and Calvard, "Picture Thresholding Using an Iterative Selection method," In IEEE Trans. Systems, Man, And Cybernetics pp. 630–632 (1978).

Rizzuto et al., "Chimeric Green Fluorescent Protein as a Tool for Visualizing Subcellular Organelles in Living Cells," Curr. Biology 5:635–642 (1995).

Spargo et al., "Spatially Controlled Adhesion, Spreading, and Differentiation of Endothelial Cells on Self–Assembled Molecular Monolayers," PNAS 91:11070–11074 (1994).

Stenger et al., "Coplanar Molecular Assemblies of Amino– and Perfluorinated Alkylsilanes: Characterization and Geometric Definition of Mammalian Cell Adhesion and Growth," Journal of the American Chemical Society 114:8435–8442 (1992).

Taylor et al., "The New Vision of Light Microscopy," American Scientist 80:322–335 (1992).

Ward et al., "Spectrophotometric Identity of the Energy transfer Chromophores in Renilla and Aequorea Green––Fluorescent Proteins," Photochem. Photobiol. 31:611–615 (1980).

Taylor et al., "Potential of Machine–Vision Light Microscopy in Toxicologic Pathology," Toxicologic Pathology 22:145–159 (1994).

Taylor et al., "Automated Interactive Microscopy: Measuring and Manipulating the Chemical and Molecular Dynamics of Cells and Tissues," Intl. Soc. for Optical Engineering 2678: 15–27 (1996).

Farkas et al., "Multimode Light Microscopy and the Dynamics of Molecules, Cells, and Tissues," Ann. Rev. Physiol. 55:785–817 (1993).

400

SYSTEM FOR CELL-BASED SCREENING

BACKGROUND OF THE INVENTION

1. Field of The Invention

This invention is in the field of introducing fluorescent reagents into or applying fluorescent reagents to cells and monitoring the fluorescence in the cells.

2. Description of The Prior Art

Drug discovery is a long, multiple step process involving the identification of specific disease targets, development of an assay based on a specific target, validation of the assay, optimization and automation of the assay to produce a screen, high throughput screening of compound libraries using the assay, hit validation and hit compound optimization. The output of this process is a lead compound that goes into preclinical and eventually clinical trials. In this process, the screening phase is distinct from the assay development phases and testing the efficacy of the compounds in living biological systems.

Performing a screen on many thousands of compounds requires parallel handling and processing of many compounds and assay component reagents. Standard high throughput screens use homogeneous mixtures of compounds and biological reagents along with some indicator compound loaded into arrays of wells in standard microtiter plates with 96 or 384 wells. The signal measured from each well, either fluorescence emission, optical density, or radioactivity, integrates the signal from all the material in the well giving an overall population average of all the molecules in the well. This type of assay is commonly referred to as a homogeneous assay.

Science Applications International Corporation (SAIC) 130 Fifth Avenue, Seattle, Wash. 98109 describes an imaging plate reader. This system uses a CCD camera to image the whole area of a 96 well plate. The image is analyzed to calculate the total fluorescence per well for homogeneous assays.

Molecular Devices, Inc. describes a system (FLIPR) which uses low angle laser scanning illumination and a mask to selectively excite fluorescence within approximately 200 microns of the bottoms of the wells in standard 96 well plates in order to reduce background when imaging cell monolayers. This system uses a CCD camera to image the whole area of the plate bottom. Although this system measures signals originating from a cell monolayer at the bottom of the well, the signal measured is averaged over the area of the well and is therefore still considered a homogeneous measurement, since it is an average response of a population of cells. The image is analyzed to calculate the total fluorescence per well for cell-based homogeneous assays.

Proffitt et. al. Cytometry 24: 204–213 (1996) describes a semiautomated fluorescence digital imaging system for quantifying relative cell numbers in situ in a variety of tissue culture plate formats, especially 96-well microtiter plates. The system consists of an epifluorescence inverted microscope with a motorized stage, video camera, image intensifier, and a microcomputer with a PC-Vision digitizer. Turbo Pascal software controls the stage and scans the plate taking multiple images per well. The software calculates total fluorescence per well, provides for daily calibration, and configures easily for a variety of tissue culture plate formats. Thresholding of digital images and reagents which only fluoresce when taken up by living cells are used to reduce background fluorescence without removing excess fluorescent reagent. For example, in this system cells are pretreated with fluorescein diacetate (FDA) and loaded into 96-well plates.

Fluorescence microscopy of cells and tissues is well known in the art. A variety of methods have been developed to image fluorescent cells in a microscope and extract information about the spatial distribution and temporal changes occurring in these cells. An article by Taylor, et al. in American Scientist 80 (1992), p. 322–335 describes many of these methods and their applications. These methods have been designed and optimized for the preparation of a few specimens for high spatial and temporal resolution imaging measurements of distribution, amount and biochemical environment of the fluorescent reporter molecules in the cells.

Treating cells with dyes and fluorescent reagents and imaging the cells is well known in the art. There is also a considerable body of prior art related to genetic engineering of cells to produce fluorescent proteins, such as modified green fluorescent protein (GFP) as a reporter molecule. The green fluorescent protein (GFP) of the jellyfish *Aequorea Victoria* is a protein with an excitation maximum at 395 nm and an emission maximum at 510 nm and does not require an exogenous factor. Uses of GFP for the study of gene expression and protein localization are discussed in more detail in papers by Chalfie et al. in Science 263 (1994), p. 12501–12504. Some properties of wild-type GFP are disclosed by Morise et al. in Biochemistry 13 (1974), p. 2656–2662, and Ward et al. in Photochem. Photobiol. 31 (1980), p. 611–615. An article by Rizzuto et al. in Curr. Biology 5 (1995), p. 635–642 discusses the use of wild-type GFP as a tool for visualizing subcellular organelles in cells. A paper by Kaether and Gerdes in Febs Letters 369 (1995), p. 267–271, reports the visualization of protein transport along the secretory pathway using wild-type GFP. The expression of GFP in plant cells is discussed by Hu and Cheng in Febs Letters 369 (1995), p. 331–334, while GFP expression in Drosophila embryos is described by Davis et al. in Dev. Biology 170 (1995), p. 726–729. U.S. Pat. No. 5,491,084 describes expressing GFP from *Aequorea victoria* in cells as a reporter molecule fused to another protein of interest. PCT/DK 96/00052 relates to methods of detecting biologically active substances affecting intracellular processes by utilizing a GFP construct having a protein kinase activation site. Numerous references are related to GFP proteins in biological systems. For example, PCT/US94/10165 describes a system for isolating cells of interest utilizing the expression of a GFP like protein. PCT/GB96/00481 describes the expression of GFP in plants. PCT/US95/01425 describes modified GFP protein expressed in transformed organisms to detect mutagenesis. U.S. Pat. Nos. 5,401,629 and 5,436,128 describe assays and compositions for detecting and evaluating the intracellular transduction of an extracellular signal. Recombinant cells that express cell surface receptors and contain reporter gene constructs that include transcriptional regulatory elements that are responsive to the activity of cell surface receptors are used.

SUMMARY OF THE INVENTION

Figure 1:
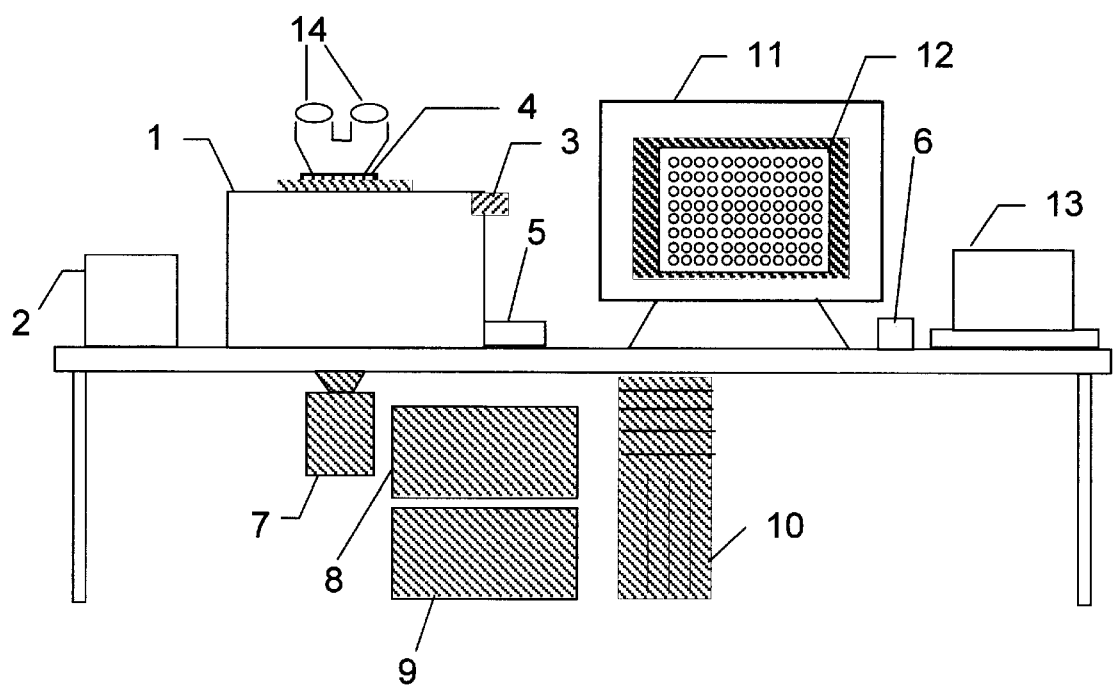
FIG. 1 shows a diagram of the components of the cell-based scanning system.

The invention relates to a computer controlled optical-mechanical system for rapidly determining the distribution, environment, or activity of fluorescently labeled reporter molecules in cells for the purpose of screening large numbers of compounds for those that specifically affect particular biological functions. The invention involves:

- providing cells containing fluorescent reporter molecules in an array of locations,
- treating the cells in the array of locations with one or more reagents,
- imaging numerous cells in each location with a fluorescence microscope,
- converting the optical information into digital data,
- utilizing the digital data to determine the distribution, environment or activity of the fluorescently labeled reporter molecules in the cells and the distribution of the cells, and
- interpreting that information in terms of a positive, negative or null effect of the compound being tested on the biological function The array of locations may be a microtiter plate or a microchip which is a microplate having cells in an array of locations. The invention includes an apparatus and a computerized method for acquiring data such as a digital frame grabber, processing, displaying and storing the data.

DETAIL DESCRIPTION OF THE INVENTION

Screening large numbers of compounds for activity with respect to a particular biological function requires preparing arrays of cells for parallel handling of cells and reagents. Standard 96 well microtiter plates which are 86 mm by 129 mm, with 6 mm diameter wells on a 9 mm pitch, are used for compatibility with current automated loading and robotic handling systems. The microplate is typically 20 mm by 30 mm, with cell locations that are 100–200 microns in dimension on a pitch of about 500 microns. Methods for making microplate are described in U.S. Ser. No. 60/018,696 filed on May 30, 1996, assigned to the same assignee. This application is incorporated herein by reference in its entirety. Microplates may consist of coplanar layers of materials to which cells adhere patterned with materials to which cells will not adhere, or etched 3-dimensional surfaces of similarly pattered materials. For the purpose of the following discussion, the terms 'well' and 'microwell' refer to a location in an array of any construction to which cells adhere and within which the cells are imaged. Microplates also include fluid delivery channels in the spaces between the wells. The smaller format of a microplate increases the overall efficiency of the system by minimizing the quantities of the reagents, storage and handling during preparation and the overall movement required for the scanning operation. In addition, the whole area of the microplate can be imaged more efficiently, allowing a second mode of operation for the microplate reader as described later in this document.

Those skilled in this art will recognize a wide variety of ways to make and deliver fluorescent reporter molecules to cells. For example, fluorescently labeled biomolecules such as proteins, phospholipids and DNA hybridizing probes, as well as fluorescent reagents specifically synthesized with particular chemical properties of binding or association have been used as fluorescent reporter molecules. Fluorescently labeled antibodies are particularly useful reporter molecules due to their high degree of specificity for attaching to a single molecular target in a mixture of molecules as complex as a cell, tissue or extract of either.

Fluorescently labeled reporter molecules are useful for determining the location, amount and chemical environment of the reporter. For example, whether the reporter is in a lipophilic membrane environment or in a more aqueous environment can be determined. The pH environment of the reporter can be determined. It can be determined whether a reporter having a chelating group is bound to an ion, such as $Ca^{++}$, or not.

Those skilled in the art will recognize a wide variety of ways to measure fluorescence. For example, some fluorescent reporter molecules exhibit a charge in excitation or emission spectra, some exhibit resonance energy transfer where one fluorescent reporter looses fluorescence, while a second gains in fluorescence, some exhibit a loss (quenching) or appearance of fluorescence, while some report rotational movements.

As mentioned earlier, see Description of the Prior Art above, a cell can be genetically engineered to express reporter molecules such as GFP coupled to a protein of interest. Using the method and systems of the present invention permits the determination of the site and extent of activity of the protein in the cells.

FIG. 1 is a schematic diagram of the system for measuring the distribution, environment, or activity of fluorescent reporter molecules in cells. An inverted fluorescent microscope 1 is a Zeiss Axiovert inverted fluorescence microscope which uses standard objectives with magnification of 1–100x to the camera, and a white light source (e.g. 100 W mercury-arc lamp or 75W xenon lamp) with power supply 2. There is an XY stage 3 to move the plate 4 in the XY direction over the microscope objective. A Z-axis focus drive 5 moves the objective in the Z direction for focusing. A joystick 6 provides for manual movement of the stage in the XYZ direction. A high resolution digital camera 7 acquires images from each well or location on the plate. 8 is a camera power supply. 9 is an automation controller and 10 is a central processing unit. The PC 11 provides a display 12 and has associated software. The printer 13 provides for printing of a hard copy record. 14 are the microscope oculars.

Figure 2:
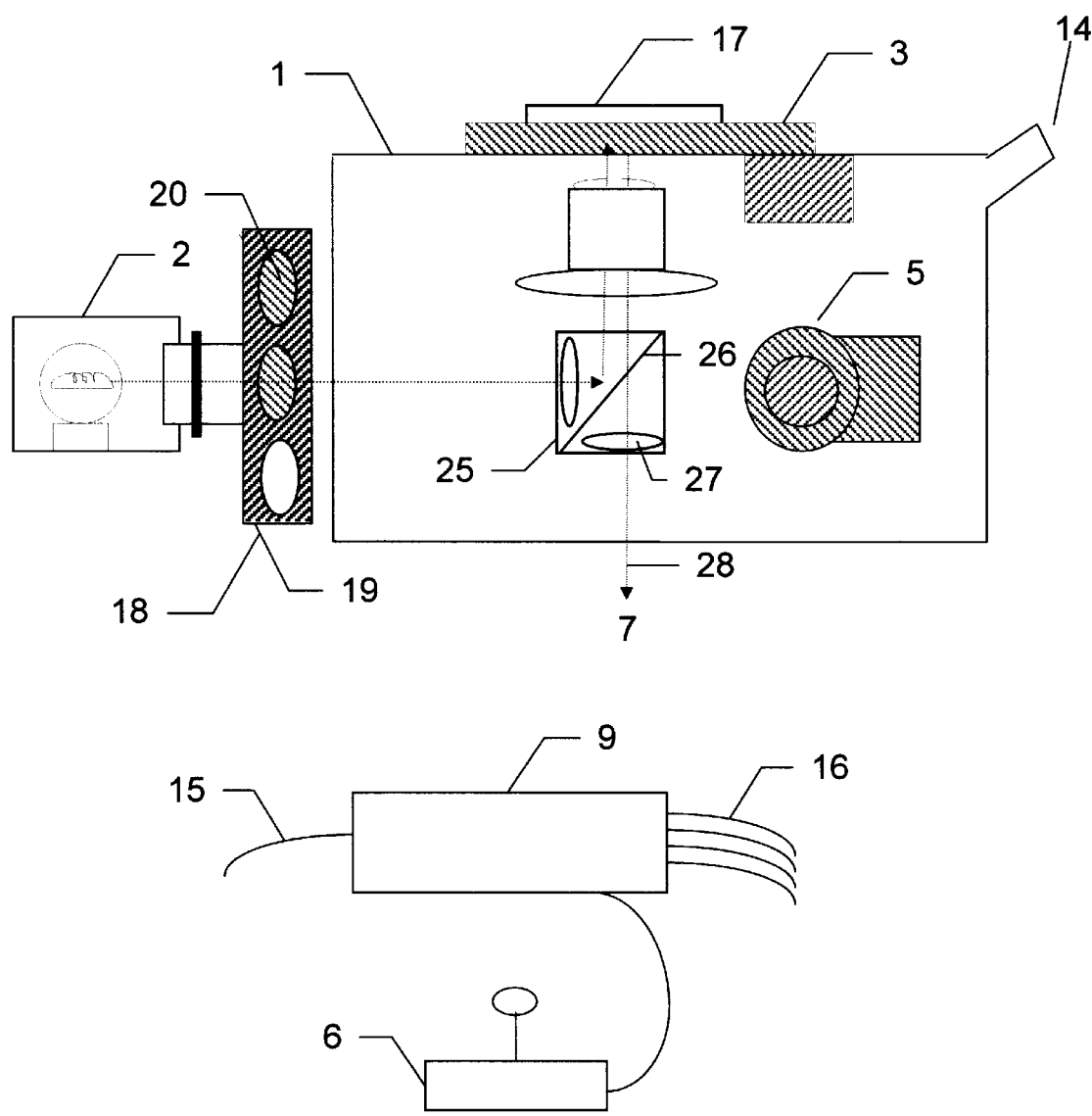
FIG. 2 shows a schematic of the microscope subassembly

FIG. 2 is a schematic of the microscope assembly 1 showing in more detail the XY stage 3, Z-axis focus drive 5, joystick 6, light source 2, automation controller 9, oculars 14. 15 and 16 are cables to the computer and microscope, respectively. In addition, FIG. 2 shows a 96 well microtiter plate 17 which is moved on the XY stage 3 in the XY direction. Light from the light source 2 passes through the PC controlled shutter 18 to a motorized filter wheel 19 with excitation filters 20. The light passes into filter cube 25 which has a dichroic mirror 26 and an emission filter 27. Excitation light reflects off the dichroic mirror to the wells in the microtiter plate 17 and fluorescent light 28 passes through the dichroic mirror 26 and the emission filter 27 and to the digital camera 7.

Figure 3:
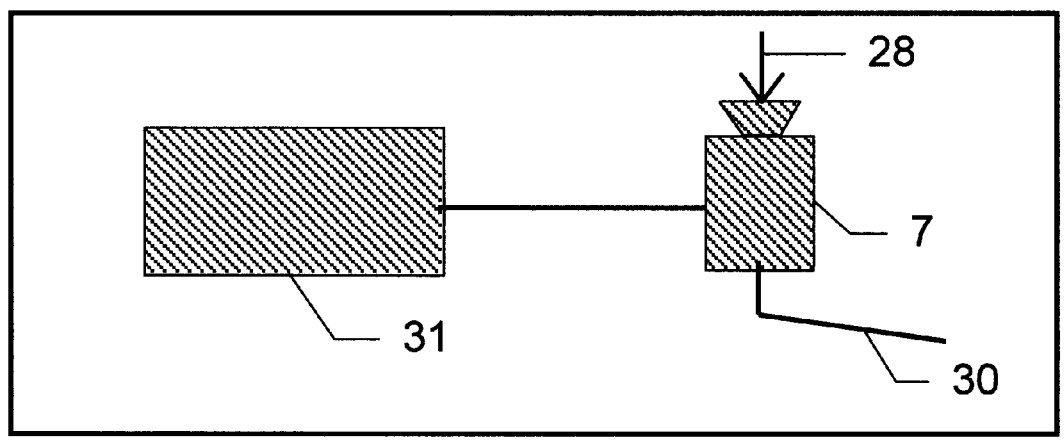
FIG. 3 shows the camera subassembly

FIG. 3 shows a schematic drawing of the camera assembly. The digital camera 7, which contains an automatic shutter for exposure control, receives fluorescent light 28 from the microscope assembly. A digital cable 30 transports digital signals to the computer. 31 is the camera power supply.

Figure 4:
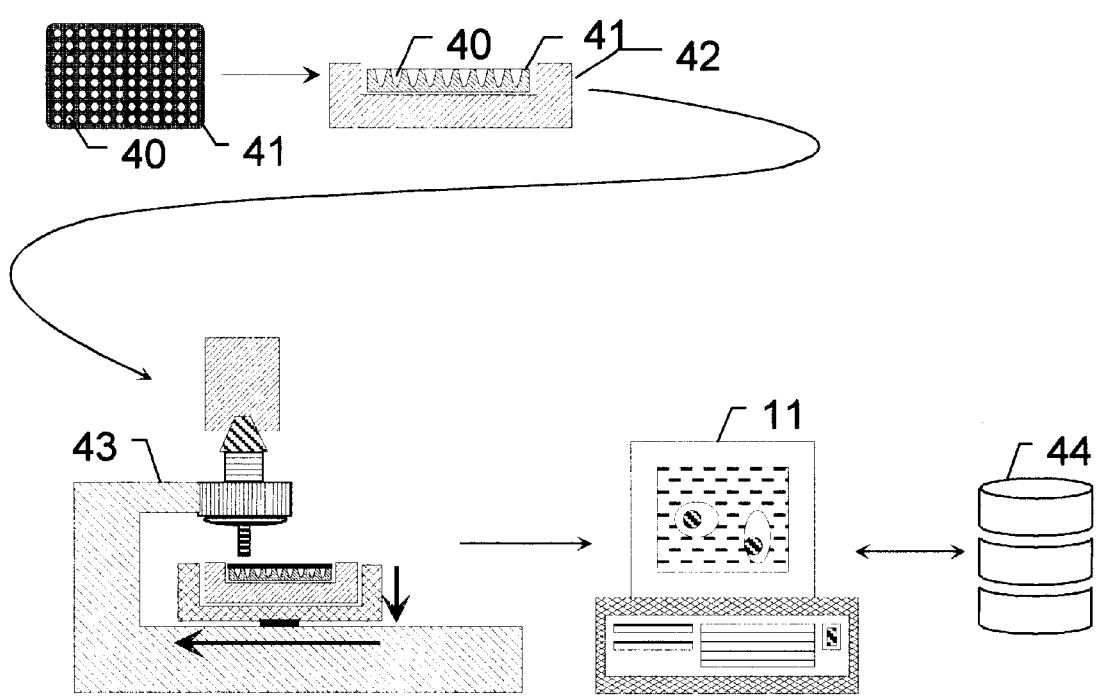
FIG. 4 illustrates cell scanning system process
Figure 5:
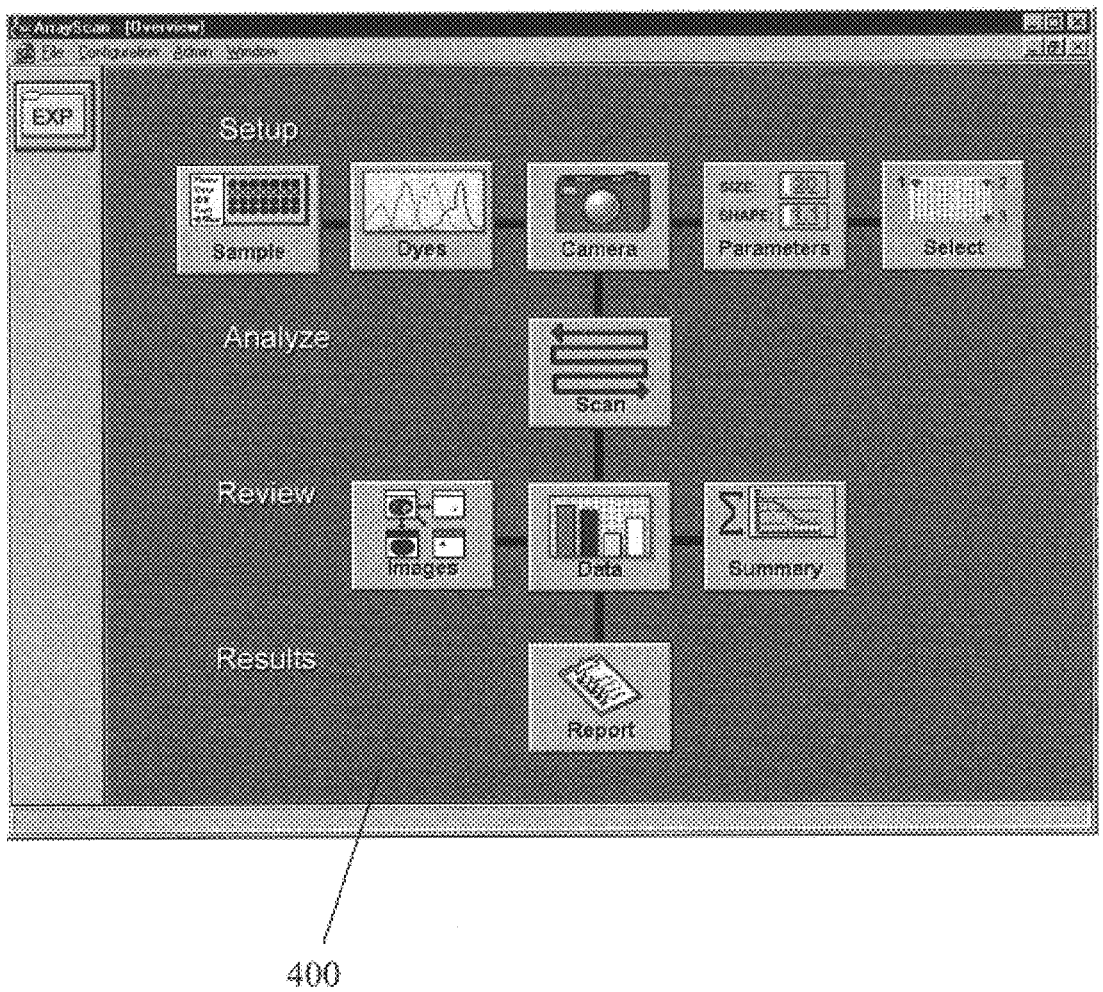
FIG. 5 illustrates a user interface showing major functions to guide the user

FIG. 4 illustrates an alternative embodiment of the invention in which cells are in microwells 40 on a microplate 41. Typically the microplate is 20 mm by 30 mm as compared to a standard 96 well microtiter plate which is 86 mm by 129 mm. The microplate chamber 42 serves as a microfluidic delivery system for the addition of compounds to cells. The microplate 41 in the microplate chamber 42 is placed in an XY microplate reader 43. Digital data is processed as described above. The small size of this microplate system increases throughput, minimizes reagent volume and provides for the ability to control the distribution and placement of cells for fast and precise cell-based analysis. This information can be displayed on a PC screen 11 and made part of a bioinformatics data base 44. This data base is an important part of the present invention because it not only permits storage and retrieval of data obtained through the methods of this invention, but also permits acquisition and storage of external data relating to cells. FIG. 5 is a PC display which illustrates the operation of the software.

In addition to the advantages cited earlier, the higher density array of cells on a microplate allows the microplate reader to image the whole microplate at a low resolution of a few microns per pixel for high throughput and image particular locations on the microplate at a higher resolution of less than 0.5 microns per pixel for higher precision. These two resolution modes improve the overall throughput of the system.

Figure 7:
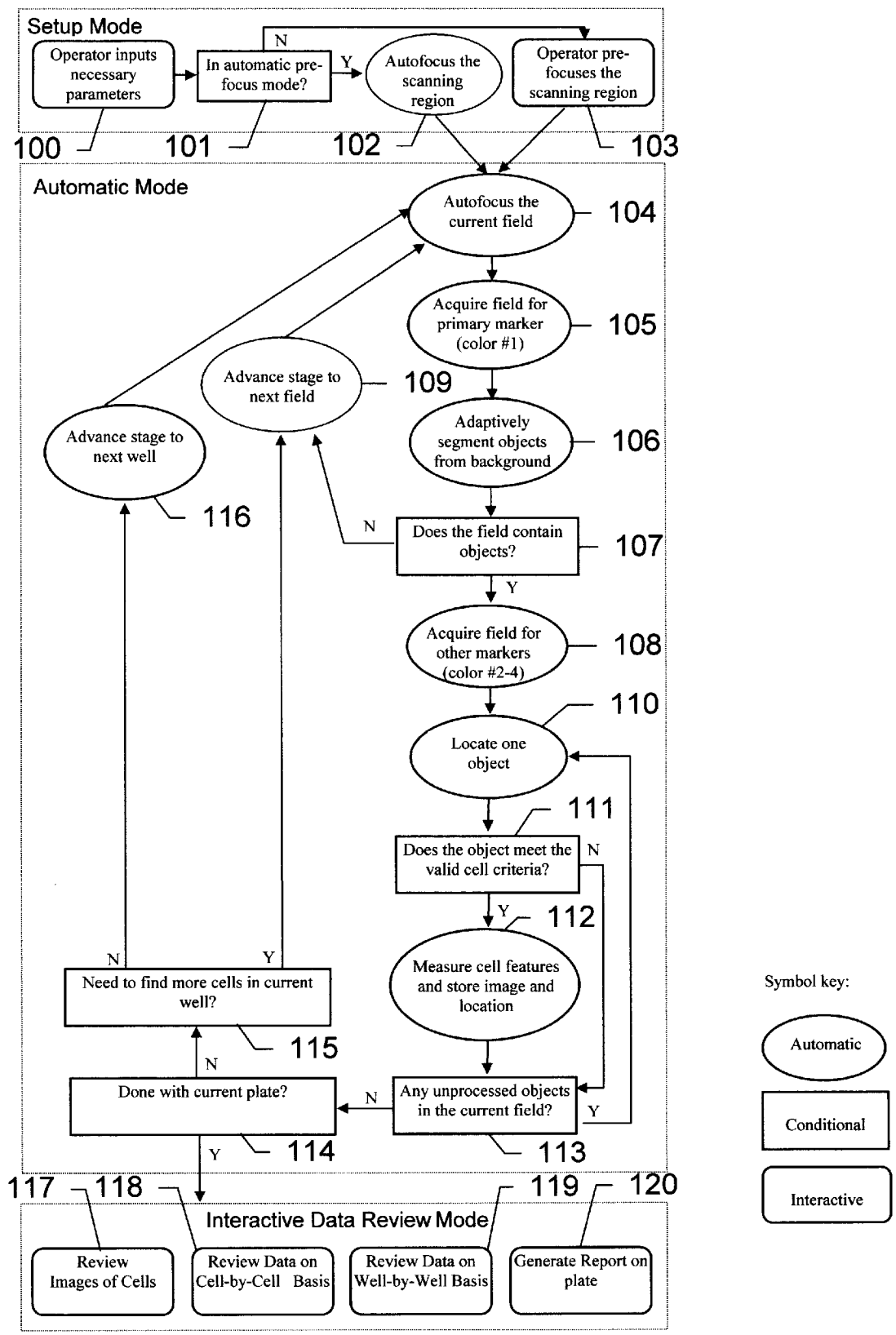
FIG. 7 flow chart of processing step for the cell-based scanning system

Referring to FIG. 7, at the start of an automated scan, the operator enters information 100 that describes the sample, specifies the filter settings and fluorescent channels to match the biological labels being used and the information sought and then adjusts the camera settings to match the sample brightness. For flexibility to handle a range of samples, the software next allows selection of various parameter settings used to identify nuclei, cytoplasm, different fluorescent reagents, cell selection settings and number of cells to be analyzed per well. These parameters are stored in the system's database for easy retrieval for each automated run. The system's interactive cell identification mode simplifies the selection of morphological parameter limits such as the range of size, shape, and intensity of cells to be analyzed. The user specifies which wells of the plate the system will scan and how many fields or how many cells to analyze in each well. Depending on the setup mode selected by the user at step 101, the system either automatically pre-focuses the region of the plate to be scanned using an autofocus procedure to "find focus" of the plate 102 or the user interactively pre-focuses 103 the scanning region by selecting three "tag" points which defines the rectangular area to be scanned by the system. A least-squares fit "focal plane model" is then calculated by the system from these tag points to estimate the focus of each well during a an automated scan. The focus of each well is estimated by interpolating from the focal plane model during a scan.

During an automated scan, the software dynamically displays the status of scan in progress such as the number of cells that have been analyzed, the current well that is being analyzed, and images of each independent wavelength as they are acquired, and the result of the screen for each well as it is acquired. The plate 4 is scanned in a serpentine style as the software automatically moves the motorized microscope XY stage 3 from well to well and field to field within each well of a 96-well plate. Those skilled in the programming art will recognize how to adapt software for scanning of other microplate formats such as 24, 48, and 384 well plates. The scan pattern of the entire plate as well as the scan pattern of fields within each well are programmed. The system adjusts sample focus with an autofocus procedure 104 through the Z axis focus drive 5, controls filter selection via a motorized filter wheel 19 and acquires and analyzes images of up to four different colors ("channels" or "wavelengths").

The autofocus procedure is called at a user selected frequency, typically for the first field in each well and then once every 4 to 5 fields within each well. The autofocus procedure calculates the starting Z-axis point by interpolating from the pre-calculated plane focal model. Starting a programmable distance above or below this set point, the procedure moves the mechanical Z-axis through a number of different positions, acquires an image at each, and finds the maximum of a calculated focus score that estimates the contrast of each image. The Z position of the image with the maximum focus score determines the best focus for a particular field. Those skilled in the art will recognize this as a variant of automatic focusing algorithms as described in the prior art in Harms et al. in Cytometry 5 (1984), p. 236–243, Groen et al. in Cytometry 6 (1985), p. 81–91, and Firestone et al. in Cytometry 12 (1991), p. 195–206.

For acquisition of images, the camera's 7 exposure time is separately adjusted for each dye to ensure a high-quality image from each channel. Software procedures can be called, at the user's option, to correct for registration shifts between wavelengths by accounting for linear (X and Y) shifts between wavelengths before making any further measurements. The electronic shutter 18 is controlled so that sample photo-bleaching is kept to a minimum. Background shading and uneven illumination can also be corrected by the software using algorithms known in the prior art.

In one channel, images are acquired of a primary marker 105 (typically cell nuclei counterstained with DAPI or PI fluorescent dyes) which are segmented ("identified") using an adaptive thresholding procedure. The adaptive thresholding procedure 106 is used to dynamically select the threshold of an image for separating cells from the background. The staining of cells with fluorescent dyes can vary to an unknown degree across cells in a microtiter plate sample as well as within images of field of cells within each well of a microtiter plate. This variation can occur due to sample preparation and/or as a result of the nature of cell biology. A global threshold is calculated for the complete image to separate the cells from background. The global adaptive techniques used in the system are variants of those described in prior art in Kittler et al. in Computer Vision, Graphics, and Image Processing 30 (1985), p. 125–147, Ridler et al. in IEEE Trans. Systems, Man, and Cybernetics (1978), p. 630–632. These global adaptive thresholding techniques account for field to field variation. Another adaptive thresholding algorithm in the system utilizes local region thresholding in contrast to global image thresholding. Image analysis of local regions in the image leads to better overall segmentation since staining of cell nuclei (as well as other labeled components) can vary across an image. The global/local processing model increases throughout and improves cell segmentation. Using this global/local procedure, a reduced resolution image (reduced in size by a factor of 2 to 4) is first globally segmented (using adaptive thresholding) to find regions of interest in the image. These regions then serve as guides to more fully analyze the same regions at full resolution. A more localized threshold is then calculated (using again adaptive thresholding) for each region of interest.

The output of the segmentation procedure is a binary mask wherein the objects are white and the background is black. This binary image, also called a mask in the prior art, is used to determine if the field contains objects 107. The mask is labeled with a blob labeling algorithm whereby each object (or blob) has a unique number assigned to it. Morphological features, such as area and shape, of the blobs are used to differentiate blobs likely to be cells from those that are considered artifacts. The user pre-sets the morphological selection criteria by either typing in known cells morphological features or by using the interactive training utility. If objects of interest are found in the field, images are acquired for all other active channels 108, otherwise the stage is advanced to the next field 109 in the current well. Each object of interest is located in the image for further analysis 110. The software determines if the object meets the criteria for a valid cell nucleus 111 by measuring its morphological features (size and shape). For each valid cell, the XYZ stage location is recorded, a small image of the cell is stored, and features are measured 112. The cell scanning system can perform multiple tests on cellular samples by applying a number of analysis methods simultaneously to measure features at multiple wavelengths including:

1. the total fluorescent intensity within the cell nucleus for colors 1–4

2. the area of the cell nucleus for color 1 (the primary marker)

3. the shape of the cell nucleus for color 1 is described by three shape features:

a) perimeter squared area b) box area ratio c) height width ratio 4. the average fluorescent intensity within the cell nucleus for colors 1–4 (i.e. #1 divided by #2)

Figure 8:
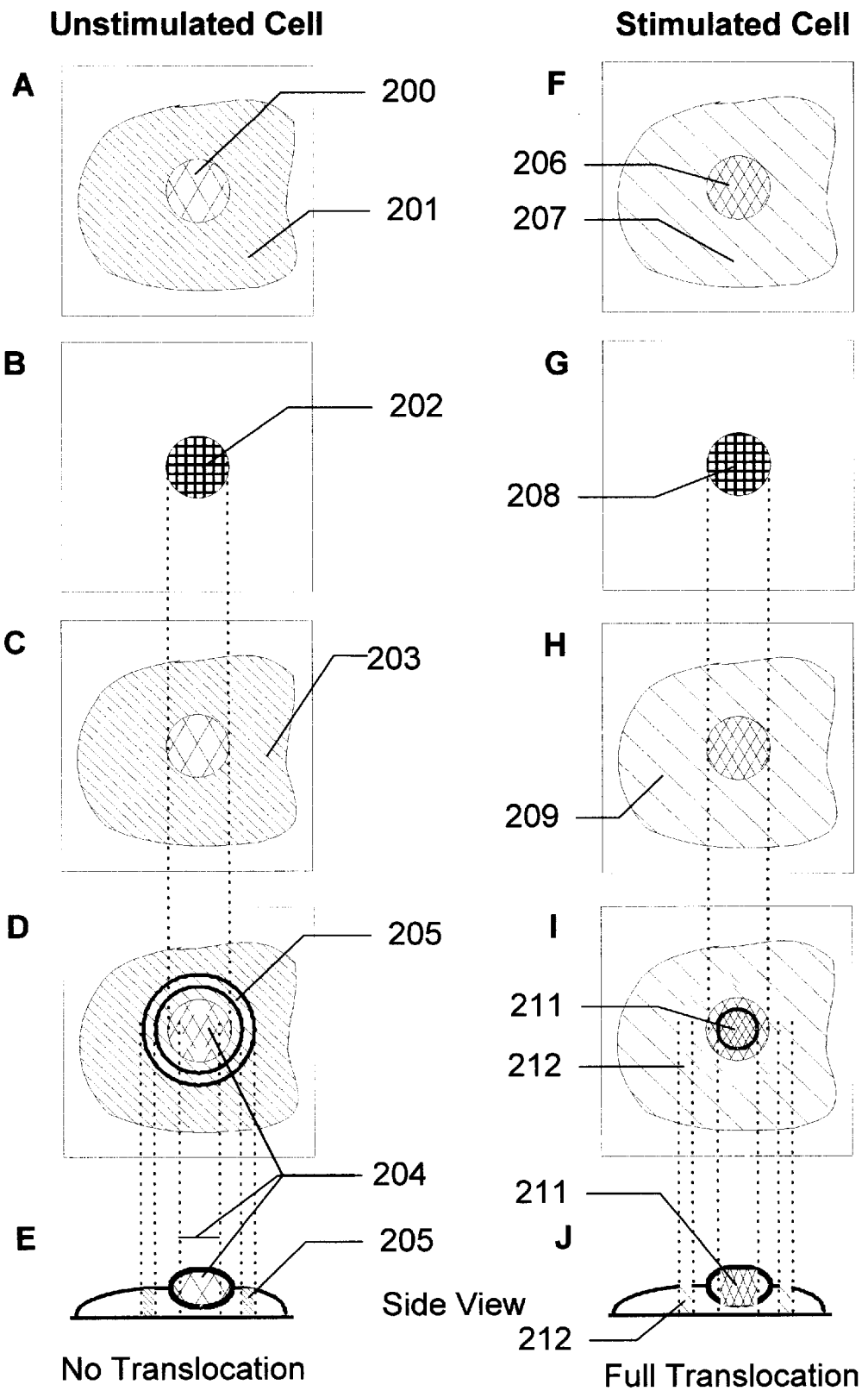
FIGS. 8 A–J illustrates the strategy of the Nuclear Translocation Assay

5. the total fluorescent intensity of a ring outside the nucleus (see FIG. 8) that represents fluorescence of the cell's cytoplasm (cytoplasmic mask) for colors 2–4

6. the area of the cytoplasmic mask 7. the average fluorescent intensity of the cytoplasmic mask for colors 2–4 (i.e. #5 divided by #6)

8. the ratio of the average fluorescent intensity of the cytoplasmic mask to average fluorescent intensity within the cell nucleus for colors 2–4 (i.e. #7 divided by #4)

9. the difference of the average fluorescent intensity of the cytoplasmic mask and the average fluorescent intensity within the cell nucleus for colors 2–4 (i.e. #7 minus #4)

10. the number of fluorescent domains (also call spots, dots, or grains) within the cell nucleus for colors 2–4

Features 1 through 4 are commonly used in a variety of image analysis applications and are well known in prior art. Features 5–9 have been developed specifically to provide measurements of a cell's fluorescent molecules within the local cytoplasmic region of the cell and the translocation (i.e. movement) of fluorescent molecules from the cytoplasm to the nucleus. These screen specific features are used for analyzing cells in microplates for the inhibition of nuclear translocation. Inhibition of nuclear translocation of transcription factors provides a novel approach to screening intact cells. An automated screen of an inhibitor of NF-κB translocation has been successfully performed. A specific algorithm measures the amount of NF-κB probe in the nuclear region (feature 4) versus the local cytoplasmic region (feature 7) of each cell. Quantification of the difference between these two sub-cellular compartments provides a measure of cytoplasm-nuclear translocation (feature 9).

Feature 10 is used for counting of DNA or RNA probes within the nuclear region in colors 2–4. For example, DNA probes are commercially available for identifying the centromeres of specific chromosomes. Cells are three-dimensional in nature and when examined at a high magnification under a microscope one probe may be in-focus while another may be completely out-of-focus. The cell screening system has a procedure for detecting three-dimensional probes in nuclei by acquiring images from multiple focal planes. The software moves the Z-axis motor drive 5 in small steps where the step distance is user selected to account for a wide range of different nuclear diameters. At each of the focal steps, an image is acquired. The maximum gray-level intensity from each pixel in each image is found and stored in a resulting maximum projection image. The maximum projection image is then used to count the probes. The above algorithm work well in counting probes that are not stacked directly above or below another one. To account for probes stacked on top of each other in the Z-direction, users can select an option to improve the counting of probes by analyzing probes in each of the focal planes acquired. In this mode, the scanning system performs the maximum plane projection algorithm as discussed above, detects probe regions of interest in this image, then further analyzes these regions in all the focal plane images.

After measuring cell features 112, the systems checks if there are any unprocessed objects in the current field 113. If there are any unprocessed objects, it locates the next object 110 and checks if it meets the criteria for a valid cell nucleus 111 and measures its features. After it the system has processed all the objects in the current field, it checks if it is done with the current plate 114. If the system is not done with the current plate, it check if it needs to find more cells in the current well 115. If it needs to find more cells in the current well it advances the XYZ stage to the next field within the current well 109 or it advances the stage to the next well 116 of the plate.

After a scan of a plate is complete, images and data can be reviewed with the system's image review, data review, and summary review facilities. All images, data, and settings from a scan are archived in the system's database for later review. Users can review the images alone of every cell analyzed by the system with an interactive image review procedure 117. The user can review data on a cell-by-cell basis using a combination of interactive graphs, a data spreadsheet of features measured, and images of all the fluorescent channels of a cell of interest with the interactive cell-by-cell data review procedure 118. Graphical plotting capabilities are provided in which data can be analyzed via interactive graphs such as histograms and scatter plots. Users can review summary data that are accumulated and summarized for all cells within each well of a plate with an interactive well-by-well data review procedure 119. Hard copies of graphs and images can be printed on a wide range of standard printers. All images and data are stored in a the system's database for archival and retrieval or for interface with a network laboratory management information system. Data can also be exported to other third-party statistical packages to tabulate results and generate other reports.

As a final phase of a complete scan, reports can be generated on one or more statistics of features measured. Users can generate a graphical report of data summarized on a well-by-well basis for the scanned region of the plate using an interactive report generation procedure 120. This report includes a summary of the statistics by well in tabular and graphical format and identification information on the sample. The report window allows the operator to enter comments about the scan for later retrieval. Multiple reports can be generated on many statistics and be printed with the touch of one button. Reports can be previewed for placement and data before being printed.

EXAMPLE SCREEN 1

Automated Screen for Compounds that Induce or Inhibit Nuclear Translocation of a DNA Transcription Factor Regulation of transcription of some genes involves activation of a transcription factor in the cytoplasm, resulting in that factor being transported into the nucleus where it can initiate transcription of a particular gene or genes. This change in transcription factor distribution is the basis of a screen for the cell-based screening system to detect compounds which inhibit or induce transcription of a particular gene or group of genes. A general description of the screen is given followed by a specific example.

The distribution of the transcription factor is determined by labeling the nuclei with a DNA specific fluorophore like Hoechst 33423 and the transcription factor with a specific fluorescent antibody. After autofocusing on the Hoechst labeled nuclei, an image of the nuclei is acquired in the cell-based screening system at 20× magnification and used to create a mask by one of several optional thresholding methods. The morphological descriptors of the regions defined by the mask are compared with the user defined parameters and valid nuclear masks are identified and used with the following algorithm to extract transcription factor distributions. Each valid nuclear mask is eroded to define a slightly smaller nuclear region. The original nuclear mask is then dilated in two steps to define a ring shaped region around the nucleus, which represents a cytoplasmic region. The average antibody fluorescence in each of these two regions is determined, and the difference between these averages is defined as the NucCyt Difference. Two examples of determining nuclear translocation are discussed below and illustrated in FIGS. 8A–J. FIG. 8A illustrates an unstimulated cell with its nucleus 200 labeled with a blue fluorophore and a transcription factor in the cytoplasm 201 labeled with a green fluorophore. FIG. 8B illustrates the nuclear mask 202 derived by the cell-based screening system. FIG. 8C illustrates the cytoplasm 203 of the unstimulated cell imaged at a green wavelength. FIG. 8D illustrates the nuclear mask 202 is eroded (reduced) once to define a nuclear sampling region 204 with minimal cytoplasmic distribution. The nucleus boundary 202 is dilated (expanded) several times to form a ring that is 2–3 pixels wide that is used to define the cytoplasmic sampling region 205 for the same cell. FIG. 8E further illustrates a side view which shows the nuclear sampling region 204 and the cytoplasmic sampling region 205. Using these two sampling regions, data on nuclear translocation can be automatically analyzed by the cell-based screening system on a cell by cell basis. FIGS. 8F–J illustrates the strategy for determining nuclear translocation in a stimulated cell. FIG. 8F illustrates a stimulated cell with its nucleus 206 labeled with a blue fluorophore and a transcription factor in the cytoplasm 207 labeled with a green fluorophore. The nuclear mask 208 in FIG. 8G is derived by the cell based screening system. FIG. 8H illustrates the cytoplasm 209 of a stimulated cell imaged at a green wavelength. FIG. 8I illustrates the nuclear sampling region 211 and cytoplasmic sampling region 212 of the stimulated cell. FIG. 8J further illustrates a side view which shows the nuclear sampling region 211 and the cytoplasmic sampling region 212.

Figure 9:
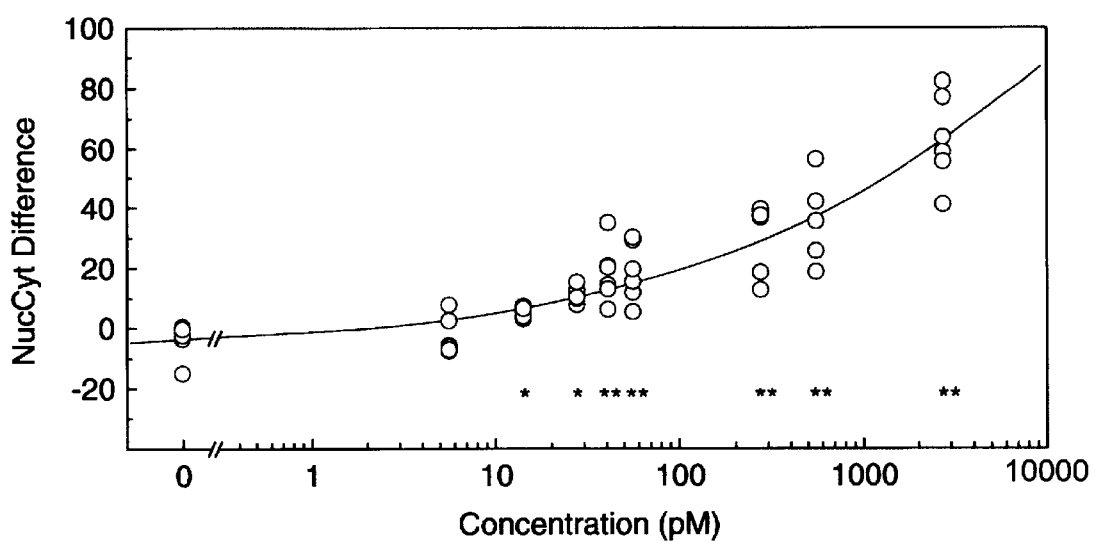
FIG. 9 is example data from a known inhibitor of translocation
Figure 10:
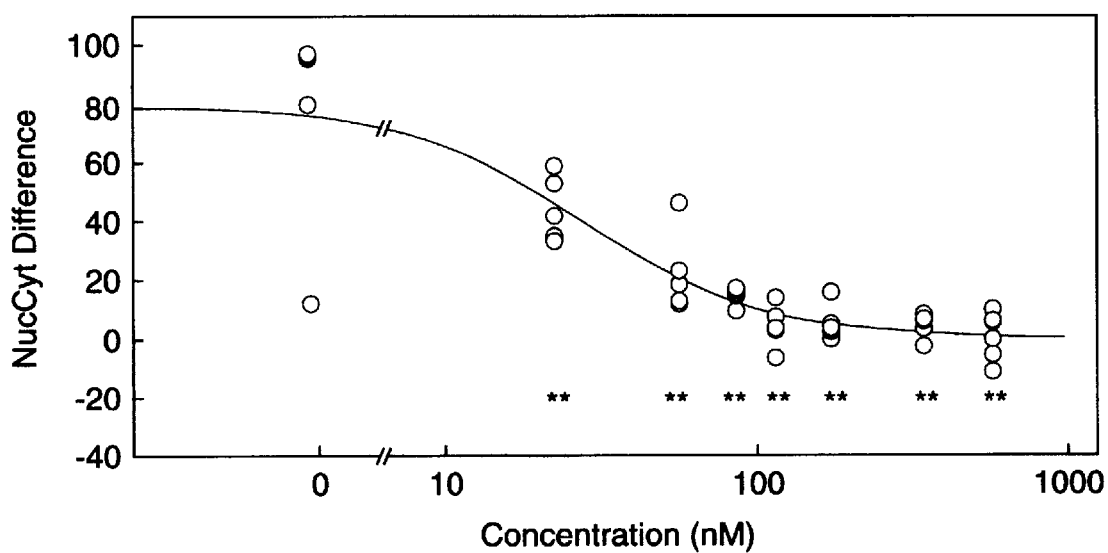
FIG. 10 is example data from a known stimulator of translocation

A specific application of this method has been used to validate this method as a screen. A human chondrocyte cell line was plated in 96 well microtiter plates. Some rows of wells were titrated with IL-1α, a known inducer of the nuclear transcription factor NF-κB. The cells were then fixed and stained by standard methods with a fluorescein labeled antibody to NF-κB, and Hoechst 33423. The cell-based screening system was used to acquire and analyze images from this plate and the NucCyt Difference was found to be strongly correlated with the amount of IL-1α added to the wells as illustrated in FIG. 9. In a second experiment, an antagonist to the receptor for IL-1, IL-1RA was titrated in the presence of IL-1α, progressively inhibiting the translocation induced by IL-1α. The NucCyt Difference was found to strongly correlate with this inhibition of translocation, as well as illustrated in FIG. 10.

Additional experiments have shown that the NucCyt Difference gives consistent results over a wide range of cell densities and reagent concentrations, and can therefore be routinely used to screen compound libraries for specific nuclear translocation activity. Furthermore, the same method can be used with antibodies to other transcription factors, or GFP-transcription factor chimeras, in living and fixed cells, to screen for effects on the regulation of transcription of this and other genes.

Figure 6:
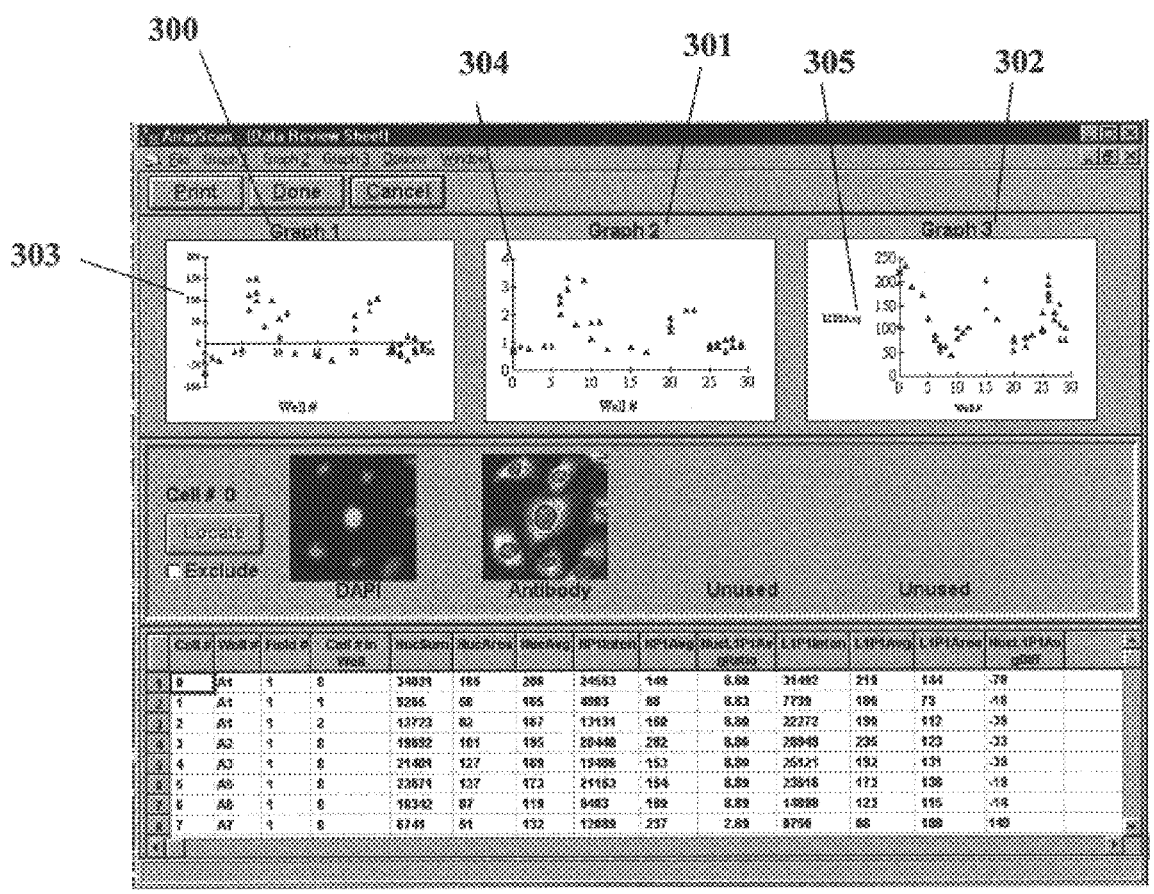
FIG. 6 illustrates data presentation on screen

FIG. 6 is a representative display on a PC screen of data which was obtained in accordance with Example 1. Graph 1 300 plots the difference between the average antibody fluorescence in the nuclear sampling region and cytoplasmic sampling region, NucCyt Difference verses Well #. Graph 2 301 plots the average fluorescence of the antibody in the nuclear sampling region, NP1 average, versus the Well #. Graph 3 302 plots the average antibody fluorescence in the cytoplasmic sampling region, LIP1 average, versus Well #. The software permits displaying data from each cell. For example, FIG. 6 shows a screen display, the nuclear image, and the fluorescent antibody image for cell #14.

NucCyt Difference referred to in graph 1 303 of FIG. 6 is the difference between the average cytoplasmic probe (fluorescent reporter molecule) intensity and the average nuclear probe (fluorescent reporter molecule) intensity. The invention provides a computer means for converting the digital signal from the camera into this parameter and for plotting the parameter verses the well number.

NP1 average referred to in graph 2 304 of FIG. 6 is the average of cyloplasmic probe (fluorescent reporter molecule) intensity within the nuclear sampling region. The invention provides a computer means for converting the digital signal from the camera into this parameter and for plotting the parameter verses the well number.

L1P1 average referred to in graph 3 305 of FIG. 6 is the average probe (fluorescent reporter molecule) intensity within the cytoplasmic sampling region. The invention provides a computer means for converting the digital signal from the camera into this parameter and for plotting the parameter verses the well number.

EXAMPLE SCREEN 2

Automated Screen for Compounds that Induce or Inhibit Hypertrophy in Cardiac Myocytes Hypertrophy in cardiac myocytes has been associated with a cascade of alterations in gene expression and can be characterized in cell culture by an alteration in cell size, that is clearly visible in adherent cells growing on a coverslip. Preliminary experiments indicate that a screen can be implemented using the following strategy. Myocytes cultured in 96 well plates, can be treated with various compounds and then fixed and labeled with a fluorescent antibody to a cell surface marker and a DNA label like Hoechst. After focusing on the Hoechst labeled nuclei, two images are acquired, one of the Hoechst labeled nuclei and one of the fluorescent antibody. The nuclei are identified by thresholding to create a mask and then comparing the morphological descriptors of the mask with a set of user defined descriptor values. Local regions containing cells are defined around the nuclei. The limits of the cells in those regions are then defined by a local dynamic threshold operation on the same region in the fluorescent antibody image. A sequence of erosions and dilations is used to separate slightly touching cells and a second set of morphological descriptors is used to identify single cells. The area of the individual cells is tabulated in order to define the distribution of cell sizes for comparison with size data from normal and hypertrophic cells. In addition, a second fluorescent antibody to a particular cellular protein, such as one of the major muscle proteins actin or myosin can included. Images of this antibody can be acquired and stored with the above images, for later review, to identify anomalies in the distribution of these proteins in hypertrophic cells, or algorithms can be developed to automatically analyze the distributions of the labeled proteins in these images.

Additional Screens

Those skilled in the art will recognize a wide variety of distinct screens that can be developed. There is a large and growing list of known biochemical and molecular processes in cells that involve translocations or reorganizations of specific components within cells. The signaling pathway from the cell surface to target sites within the cell involves the translocation of plasma membrane-associated proteins to the cytoplasm. For example, it is known that one of the src family of protein tyrosine kinases, pp60c-src, translocates from the plasma membrane to the cytoplasm upon stimulation of fibroblasts with platelet-derived growth factor (PDGF). In contrast, some cytoplasmic components translocate from the cytoplasm to the plasma membrane upon stimulation of cells. For example, it is known that the GTP-binding proteins of the Rho family are maintained as cytoplasmic complexes with RhoGDI in resting cells, but are released and translocate to plasma membrane during cell activation. In addition, specific organelles, such as components of the cytoskeleton, nuclear envelope, chromatin, golgi apparatus, mitochondria, and endosomes are reorganized in response to specific stimuli. Finally, the targets for screening can themselves be converted into fluorescence-based reagents that report molecular changes including ligand-binding and post-translocational modifications.

REFERENCES

1) C. S. Dulcey, J. H. Georger, V. Krauthamer, T. L. Fare, D. A. Stenger, and J. M. Calvert, "Deep UV Photochemistry of Chemisorbed Monolayers: Fabrication of Patterned Co- Planar Molecular Assemblies", Science, 1991, 252, 551.
2) J. M. Calvert, "Lithographically Patterned Self-Assembled Films", in Thin Films, Vol. 20—Organic Thin Films and Surfaces: Directions for the in the Nineties", A. Ulman, Ed., Academic Press, Boston (1995), 109–141.
3) C. S. Dulcey, J. H. Georger, M. S. Chen, S. McElvany, C. E. O'Ferrall, V. I. Benezra, and J. M. Calvert, "Photochemistry and Patterning of Self-Assembled Monolayer Films Containing Aromatic Hydrocarbon Functional Groups", Langmuir, 1996, 12, 1638.
4) W. J. Dressick, C. S. Dulcey, M. S. Chen, and J. M. Calvert "Photochemical Studies of (Aminoethylaminomethyl) phenethyltrimethoxysilane (PEDA) Self-Assembled Monolayer Films", Thin Solid Films, 1996, in press.
5) D. A. Stenger, J. H. Georger, C. S. Dulcey, J. J. Hickman, A. S. Rudolph, T. B. Nielsen, S. M. McCort, and J. M. Calvert, "Coplanar Molecular Assemblies of Amino-and Perfluorinated Alkylsilanes: Characterization and Geometric Definition of Mammalian Cell Adhesion and Outgrowth", Journal of the American Chemical Society, 1992, 114, 8435.
6) B. J. Spargo, M. A. Testoff, T. Nielson, D. A. Stenger, J. J. Hickman, and A. S. Rudolph, "Spatially Controlled Adhesion, Spreading, and Differentiation of Endothelial Cells on Self-Assembled Molecular Monolayers, Proceedings of the National Academy of Sciences, 1994, 91, 11070.
7) L. A. Chrisey, P. M. Roberts, V. I. Benezra, W. J. Dressick, C. S. Dulcey, and J. M. Calvert, "Selective Attachment of Synthetic DNA to Self-Assembled Monolayer Functionalized Surfaces", Proceedings, Materials Research Society, 1994, 330, 179.
8) L. A. Chrisey, C. E. O'Ferrall, B. J. Spargo, C. S. Dulcey, and J. M. Calvert "Fabrication of Patterned DNA Surfaces", Nucleic Acids Research, 1996, 24, 3040.
9) L. A. Chrisey, G. U. Lee, and C. E. O'Ferrall, "Covalent Attachment of Synthetic DNA to Self-Assembled Monolayer Films", Nucleic Acids Research, 1996, 24, 3031.
10) S. K. Bhatia, J. L. Teixeira, M. Anderson, L. C. Shriver-Lake, J. M. Calvert, J. H. Georger, J. J. Hickman, C. S. Dulcey, P. E. Schoen, and F. S. Ligler, "Fabrication of Surfaces Resistant to Protein Adsorption and Their Application to Two-Dimensional Proten Patterning", Analytical Biochemistry, 1993, 208, 197.
11) J. M. Calvert, G. S. Calabrese, J. F. Bohland, M. S. Chen, W. J. Dressick, C. S. Dulcey, J. H. Georger, Jr., J. Kosakowski, E. K. Pavelchek, K. W. Rhee, and L. M. Shirey, "Photoresist Channel-Constrained Electroless Metal Deposition on Ligating Self-Assembled Films", Journal of Vacuum Science and Technology, 1994, B12, 3884.
12) R. Kapur, B. J. Spargo, M. S. Chen, J. M. Calvert, and A. S. Rudolph, "Fabrication of 3-Dimensionally Textured Biomedical Polymers from Etched Silicon Substrates", Journal of Biomedical Materials Research, in press.
13) Harms, H. and Aus, H. M., "Comparison of Digital Focus Criteria for a TV Microscope System," Cytometry 5 (1984), p. 236–243
14) Groen, F. A., Young, I. T., and Ligthart, G., "A Comparison of Different Focus Functions for Use in Autofocus Algorithms," Cytometry 6 (1985), p. 81–91
15) Firestone, L., Cook, K., Talsania, N., Preston, K., "Comparison of Autofocus Methods for Automated microscopy," Cytometry 12 (1991), p. 195–206
16) Kittler, J. and Illingworth, J., "Threshold Selection Based on a Simple Image Statistic," Computer Vision, Graphics, and Image Processing 30 (1985), p. 125–147,
17) Ridler, T. and Calvard, S. "Picture Thresholding Using an Iterative Selection Method," IEEE Trans. Systems, Man, and Cybernetics (1978), p. 630–632

What is claimed is:

1. An automated method for analyzing cells comprising;
a) providing an array of locations which contain multiple cells, wherein the cells contain one or more fluorescent reporter molecules;
b) scanning multiple cells in each of the locations containing cells to obtain fluorescent signals from the fluorescent reporter molecules in subcellular compartments of the cells being analyzed wherein the subcellular compartments comprise the cell nucleus and the cell cytoplasm;

c) converting the fluorescent signals into digital data;

d) utilizing the digital data to automatically make measurements, wherein the measurements are used to automatically calculate changes in the distribution, environment or activity of the fluorescent reporter molecules within or between the cell nucleus and the cell cytoplasm of the cells being analyzed, wherein the measurements comprise determining:
   i) the fluorescence intensity of reporter molecules within the cell nucleus;
   ii) the fluorescence intensity of reporter molecules within the cell cytoplasm;
   iii) the area of the cell nucleus; and
   iv) the area of the cytoplasm.

2. The method of claim 1 wherein the calculated changes comprise:
   a) changes in the fluorescence intensity of reporter molecules within the cell nucleus of the cells being analyzed;
   b) changes in the fluorescence intensity of reporter molecules within the cell cytoplasm of the cells being analyzed;
   c) changes in the ratio of the fluorescence intensity within the cell cytoplasm to the fluorescence intensity within the cell nucleus of the cells being analyzed; and
   d) changes in the difference of the fluorescence intensity within the cytoplasm and the fluorescence intensity within the nucleus of the cells being analyzed.

3. The method of claim 2 wherein the calculated changes provide a measurement of translocation of fluorescent reporter molecules from the cytoplasm to the nucleus of the cells being analyzed.

4. The method of claim 3 wherein the fluorescent reporter molecules comprise a transcription factor.

5. The method of claim 4 wherein the transcription factor comprises NF-kB.

6. An automated method for analyzing cells comprising:
   a) providing an array of locations which contain multiple cells, wherein the cells contain one or more fluorescent reporter molecules;
   b) scanning multiple cells in each of the locations containing cells to obtain fluorescent signals from the fluorescent reporter molecules in subcellular compartments of the cells, wherein the subcellular compartments comprise the cell nucleus and a subcellular compartment selected from the group consisting of the cell membrane and the cell cytoplasm;
   c) converting the fluorescent signals into digital data;
   d) utilizing the digital data to automatically make measurements, wherein the measurements are used to automatically calculate changes in the distribution, environment or activity of the fluorescent reporter molecules within or between the cell nucleus and the subcellular compartment selected from the group consisting of the cell membrane and the cell cytoplasm, wherein the digital data are captured as pixels, and wherein:
      i) the fluorescence intensity of reporter molecules within the cell nucleus defines a nuclear region, and wherein the total number of pixels within the nuclear region comprises a measure of nuclear area; and
      ii) the fluorescence intensity of reporter molecules in the subcellular compartment selected from the group consisting of the cell membrane and the cell cytoplasm defines a cytoplasmic region, and wherein the total number of pixels in the cytoplasmic region comprises a measure of the cytoplasmic area.

7. The method of claim 6 wherein the calculated changes comprise:
   (a) changes in the measure of nuclear area;
   (b) changes in the measure of cytoplasmic area; and
   (c) changes in the ratio of cytoplasmic area to nuclear area.

8. The method of claim 7 wherein the calculated changes provide a measurement of cellular hypertrophy.

* * * * *